(12) United States Patent
He et al.

(10) Patent No.: US 12,195,722 B2
(45) Date of Patent: Jan. 14, 2025

(54) INTELLIGENT MICROBIAL SAMPLE TREATMENT SYSTEM

(71) Applicant: CHONGQING CORETECH MEDICAL TECHNOLOGY CO., LTD., Chongqing (CN)

(72) Inventors: Linsheng He, Chongqing (CN); Qiang Yuan, Chongqing (CN)

(73) Assignee: CHONGQING CORETECH MEDICAL TECHNOLOGY CO., LTD., Chongqing (CN)

(*) Notice: Subject to any disclaimer, the term of this patent is extended or adjusted under 35 U.S.C. 154(b) by 860 days.

(21) Appl. No.: 17/413,963

(22) PCT Filed: Apr. 16, 2020

(86) PCT No.: PCT/CN2020/085130
§ 371 (c)(1),
(2) Date: Jun. 15, 2021

(87) PCT Pub. No.: WO2020/253345
PCT Pub. Date: Dec. 24, 2020

(65) Prior Publication Data
US 2022/0033760 A1    Feb. 3, 2022

(30) Foreign Application Priority Data

Jun. 18, 2019 (CN) .......................... 201910525808.4
Aug. 30, 2019 (CN) .......................... 201921427881.X (Continued)

(51) Int. Cl.
| | | |
|---|---|---|
| C12M 1/00 | (2006.01) | |
| C12M 1/12 | (2006.01) | |
| C12M 1/33 | (2006.01) | |

(52) U.S. Cl.
CPC ............ *C12M 45/22* (2013.01); *C12M 37/00* (2013.01); *C12M 45/02* (2013.01)

(58) Field of Classification Search
None
See application file for complete search history.

(56) References Cited

FOREIGN PATENT DOCUMENTS

| | | |
|---|---|---|
| CN | 104862215 A | 8/2015 |
| CN | 204981874 U | 1/2016 |

(Continued)

*Primary Examiner* — William H. Beisner
(74) *Attorney, Agent, or Firm* — Bayramoglu Law Offices LLC

(57) ABSTRACT

An intelligent microbial sample treatment system includes a workbench, and a sample treatment assembly, a culture medium treatment assembly, a streaking assembly and a culture medium storage assembly that are disposed on the workbench; the sample treatment assembly comprises a sample transfer device, a filling device, and a scanning device, a weight detection device, a filling location, a shaking device and waiting locations that are disposed in sequence; and the sample transfer device moves a sample cup among the scanning device, the weight detection device, the filling location, the shaking device and the waiting locations. The intelligent microbial sample treatment system disclosed by the present invention enables improvement of work efficiency and reduction of space occupation and has a reasonable structural layout and high work efficiency.

18 Claims, 10 Drawing Sheets

(30) Foreign Application Priority Data

Dec. 17, 2019 (CN) .......................... 201922266711.4
Dec. 17, 2019 (CN) .......................... 201922267972.8
Dec. 17, 2019 (CN) .......................... 201922269408.X
Dec. 25, 2019 (CN) .......................... 201922363644.8

(56) References Cited

FOREIGN PATENT DOCUMENTS

| | | |
|---|---|---|
| CN | 104862215 B | 4/2017 |
| CN | 106867869 A | 6/2017 |
| CN | 206814768 U | 12/2017 |
| CN | 208308391 U | 1/2019 |
| CN | 109294897 A | 2/2019 |
| CN | 110184181 A | 8/2019 |
| WO | 2006044424 A2 | 4/2006 |
| WO | WO-2008083439 A1 * | 7/2008 ............ C12M 33/02 |

* cited by examiner

INTELLIGENT MICROBIAL SAMPLE TREATMENT SYSTEM

CROSS REFERENCE TO THE RELATED APPLICATIONS

This application is the national phase entry of International Application No. PCT/CN2020/085130, filed on Apr. 16, 2020, which is based upon and claims priority to Chinese Patent Application No. 201922363644.8, filed on Dec. 25, 2019, Chinese Patent Application No. 201922269408.X, filed on Dec. 17, 2019, Chinese Patent Application No. 201922267972.8, filed on Dec. 17, 2019, Chinese Patent Application No. 201922266711.4, filed on Dec. 17, 2019, Chinese Patent Application No. 201921427881.X, filed on Aug. 30, 2019, and Chinese Patent Application No. 201910525808.4, filed on Jun. 18, 2019, the entire contents of which are incorporated herein by reference.

TECHNICAL FIELD

The present invention belongs to the technical field of microbiology apparatus, and relates to an intelligent microbial sample treatment system.

BACKGROUND

Microbial sample treatment is widely used for colony inoculation, culture, separation and detection, and microbial sample treatment is an important work in the aspects of medical care and public health, inspection and quarantine, disease control, food safety and the like. The Chinese patent disclosed a microbial sample treatment streaking system and method [the grant announcement number CN104862215B]; the microbial sample treatment streaking system comprises a communication unit, a mechanical unit and a circuit, the communication unit is in signal connection with the mechanical unit, and the communication unit and the mechanical unit are separately electrically connected with an external circuit; the mechanical unit comprises a sample treatment assembly, a streaking assembly, a culture medium treatment assembly and a culture medium storage assembly, the sample treatment assembly is mechanically matched with the streaking assembly to allow the streaking assembly to be dipped into a sample treated by the sample treatment assembly, the streaking assembly is mechanically matched with the culture medium treatment assembly to allow the streaking assembly which dips into liquid to carry out streaking on a culture medium treated by the culture medium treatment assembly, and the culture medium treatment assembly is mechanically matched with the culture medium storage assembly to allow the streaked culture medium to be stored in the culture medium storage assembly; and a sample control module is used for communication and control of the sample treatment assembly, a streaking control module is used for communication and control of the streaking assembly, a culture medium control module is used for communication and control of the culture medium treatment assembly, and a culture medium storage module is used for communication and control of the culture medium storage assembly.

The microbial sample treatment streaking system solves the problems of low biological safety, incapacity of operation standardization and high randomness of manual operation, but the microbial sample treatment streaking system is unreasonable in structural layout, resulting in that space occupation is large and the working efficiency is reduced to a certain degree, and a great amount of motors are used, resulting in high manufacturing cost.

SUMMARY

For the above problems existing in the prior art, an objective of the present invention is to propose an intelligent microbial sample treatment system which is reasonable in structural layout so as to improve the working efficiency.

The objective of the present invention can be fulfilled by the following technical solution:

an intelligent microbial sample treatment system comprises a workbench, and a sample treatment assembly, a culture medium treatment assembly, a streaking assembly and a culture medium storage assembly which are disposed on the workbench; the sample treatment assembly comprises a sample transfer device, a filling device, and a scanning device, a weight detection device, a filling location, a shaking device and waiting locations which are disposed in sequence, and the sample transfer device moves a sample cup among the scanning device, the weight detection device, the filling location, the shaking device and the waiting locations; and the culture medium treatment assembly comprises a culture medium loading rotary table with loading grooves, a pushing device, an opening device and a culture medium streaking rotary table with station grooves, the culture medium loading rotary table is located in front of the sample treatment assembly, the culture medium streaking rotary table is located beside the culture medium loading rotary table, and when the culture medium streaking rotary table rotates, the station grooves are sequentially close to the culture medium loading rotary table, the streaking assembly and the culture medium storage assembly.

In the intelligent microbial sample treatment system, N loading grooves are provided and distributed on the culture medium loading rotary table in an annular array, and n station grooves are provided and distributed on the culture medium streaking rotary table in an annular array; the station groove directly facing the loading groove is located at a loading station, and the pushing device is used for pushing a culture medium box in the loading groove into the station groove at the loading station; and the opening device is located at the upper portion of the station groove and used for opening the culture medium box entering the station groove. The culture medium loading rotary table carries out stepping rotation according to an angle of 360°/N, the culture medium streaking rotary table carries out stepping rotation according to an angle of 360°/n, and every time when the culture medium loading rotary table and the culture medium streaking rotary table rotate, there is one station groove directly facing the loading groove.

In the intelligent microbial sample treatment system, the loading groove is formed by a first side plate, a second side plate and a backing plate, the culture medium loading rotary table is provided with a positioning structure for positioning the first side plate, the second side plate and the backing plate, and the backing plate is provided with a penetrating hole for the pushing device to penetrate.

In the intelligent microbial sample treatment system, the positioning structure comprises a plurality of positioning protrusions separately located between two adjacent loading grooves; one side of the positioning protrusion is provided with a first mounting groove for mounting the first side plate; the other side of the positioning protrusion is provided with a second mounting groove for mounting the second side plate; one end, close to the central axis of the culture medium loading rotary table, of the positioning protrusion is provided with a limiting blocking edge; one side, facing the central axis of the culture medium loading rotary table, of the backing plate is attached to the limiting blocking edge; and a gap for the pushing device to pass through is provided between two adjacent limiting blocking edges. During mounting, firstly, the backing plate is inserted between two positioning protrusions, the backing plate is attached to the limiting blocking edge, the first side plate is inserted into the first mounting groove, the second side plate is inserted into the second mounting groove, the first side plate and the second side plate are pressed against the backing plate, and the backing plate is prevented from falling off under the pressing-against action of the first side plate and the second side plate. In order to improve stability, the first side plate, the second side plate and the backing plate are connected as a whole.

In the intelligent microbial sample treatment system, one end, away from the central axis of the culture medium loading rotary table, of the loading groove is provided with a front plate of which the lower end is pressed against the positioning protrusion, the front plate is provided with an elastic limiting plate extending into the loading groove, and the distance from the lower end of the elastic limiting plate to the bottom of the loading groove is less than the thickness of the culture medium box.

The positioning structure further comprises a pressure plate simultaneously pressing the upper ends of the first side plate, the second side plate and the backing plate and a plurality of screws for fixing the pressure plate to the culture medium loading rotary table, the screws are disposed perpendicular to the culture medium loading rotary table, and the lower ends of the screws are connected to the positioning protrusions. In order to improve stability, the first side plate, the second side plate and the backing plate are connected as a whole. The first side plate is provided with a first guide rail, the second side plate is provided with a second guide rail, and the front plate is slidably disposed on the first guide rail and the second guide rail.

In the intelligent microbial sample treatment system, the streaking assembly comprises a first-region streaking module, a second-region streaking module, a first placement seat located within the working range of the first-region streaking module and a second placement seat located within the working range of the second-region streaking module, the workbench is provided with a first driving structure, a grabbing device which is driven by the first driving structure and can move along an X axis and a Z axis and a sterilizer located in a movement region of the grabbing device, the first placement seat is located in the movement region of the grabbing device, and the workbench is further provided with a second driving structure for driving the second placement seat to move between the working range of the second-region streaking module and the movement region of the grabbing device.

When an inoculation needle in the first placement seat is disinfected, the grabbing device grabs the inoculation needle located in the first placement seat, the inoculation needle is enabled to move into the sterilizer to be disinfected under the action of the first driving structure, and after disinfection is completed, the inoculation needle is returned to the first placement seat under the action of the first driving structure and the grabbing device. When an inoculation needle in the second placement seat is disinfected, the second driving structure drives the second placement seat to move into the movement region of the grabbing device, the grabbing device grabs the inoculation needle located in the second placement seat, the inoculation needle is enabled to move into the sterilizer to be disinfected under the action of the first driving structure, after disinfection is completed, the inoculation needle is returned to the second placement seat under the action of the first driving structure and the grabbing device, and subsequently the second placement seat is returned to the working range of the second-region streaking module under the action of the second driving structure.

In the intelligent microbial sample treatment system, the first driving structure comprises a support pillar disposed on the workbench, an X-axis guide rail disposed on the support pillar, a first sliding seat slidably disposed on the X-axis guide rail, a first power unit for driving the first sliding seat to slide, a Z-axis guide rail disposed on the first sliding seat, a second sliding seat slidably disposed on the Z-axis guide rail and a second power unit for driving the second sliding seat to slide, and the grabbing device is disposed on the second sliding seat. The X-axis guide rail horizontally extends, and the Z-axis guide rail is vertically disposed beside the X-axis guide rail. When the first power unit works, the first sliding seat is driven to horizontally move on the X-axis guide rail; and when the second power unit works, the second sliding seat is driven to vertically move on the Z-axis guide rail;

wherein, the first power unit is a motor, and the motor is in transmission connection with the first sliding seat by a first ball screw pair; and the second power unit is a motor, and the motor is in transmission connection with the second sliding seat by a second ball screw pair. Or, the first power unit is a cylinder, and a piston rod of the cylinder is fixedly connected with the first sliding seat; and the second power unit is a cylinder, and a piston rod of the cylinder is fixedly connected with the first sliding seat.

In the intelligent microbial sample treatment system, the second driving structure comprises a Y-axis guide rail disposed on the workbench, a third sliding seat disposed on the Y-axis guide rail and a third power unit for driving the third sliding seat to slide, one end of the Y-axis guide rail is located in the movement region of the grabbing device, the other end of the Y-axis guide rail is located within the working range of the second-region streaking module, and the second placement seat is disposed on the third sliding seat. When the third power unit is a motor, the motor is in transmission connection with the third sliding seat by a third ball screw pair; and when the third power unit is a cylinder, a piston rod of the cylinder is fixedly connected with the third sliding seat. When the second placement seat moves into the movement region of the grabbing device, the sterilizer is located between the first placement seat and the second placement seat. Due to arrangement of the Y-axis guide rail, the second placement seat can be effectively guided to enable the second placement seat and the first driving structure to simultaneously act, the travel of the first driving structure is reduced, and time is saved, thereby improving the working efficiency wherein, the grabbing device is an electromagnet, the inoculation needle grabbed by the grabbing device comprises a needle seat, a via hole is disposed in the needle seat, an inoculation needle body capable of moving in the axial direction of the via hole is disposed in a penetrating manner in the via hole, the lower end of the inoculation needle body penetrates out of the lower end of the via hole, the upper end of the inoculation needle body penetrates out of the upper end of the via hole, a counter weight block for preventing the inoculation needle body from falling out of the via hole is disposed between the inoculation needle body and the needle seat, and the needle seat has magnetism, wherein the counter weight block is located above the via hole, the maximum lateral size of the counter weight block is larger than the hole diameter of the via hole, and a floating avoiding hole is formed in the counter weight block.

In the intelligent microbial sample treatment system, the culture medium storage assembly comprises a label printer, a culture medium storage box and a boxing module, the station groove disposed opposite to the label printer is located at a label printing station, the culture medium storage box is positioned between a streaking station and the label printing station and partially extends to the position above the culture medium streaking rotary table, the culture medium storage box is provided with a closing mechanism for closing the culture medium box moving to the label printing station from the streaking station, and the boxing module is used for moving the culture medium box between the label printing station and the culture medium storage box.

In the intelligent microbial sample treatment system, the sample cup comprises a cup body and a cup cover, and the outer wall of the cup cover has a positioning plane vertically extending; the workbench is provided with a sample cup transmission device, the sample cup transmission device is provided with a sample input rail and an abnormal sample output rail, the sample input rail is provided with a guide door, the inner side of the guide door has a limiting plane vertically extending along the conveying direction of the sample input rail, and the minimum distance from the central axis of the cup cover of the sample cup located in the sample input rail to the limiting plane is equal to the distance from the positioning plane to the central axis of the cup cover.

After the cup body is placed into the sample input rail, the cup body cannot circumferentially rotate. When the sample cup qualified in matching of the cup cover and the cup body passes through the guide door, the positioning plane is parallel to the limiting plane without interference and obstruction therebetween, and the sample cup can pass through the guide door; and when the sample cup unqualified in matching of the cup cover and the cup body passes through the guide door, the positioning plane is not parallel to the limiting plane, interference and obstruction can be generated therebetween, and the guide door prevents the sample cup from passing through.

In the intelligent microbial sample treatment system, the sample cup comprises a cup body and a cup cover, the top of the cup cover has a plurality of grooves circumferentially distributed, the workbench is also provided with a sample cup opening and closing device, and the sample cup opening and closing device comprises a moving seat, a rotating body vertically disposed in a penetrating manner in the moving seat, and a power assembly for driving the rotating body to rotate around the central axis per se; and the sample cup opening and closing device further comprises one of the following structures:

a first structure: a plurality of protrusions which are circumferentially distributed at the bottom of the rotating body and can be inserted into the corresponding grooves, the number of the grooves being larger than or equal to that of the protrusions, each protrusion having one groove disposed corresponding to the protrusion, and the rotating body being further provided with a grabbing assembly; and a second structure: a clamping jaw which is disposed at the bottom of the rotating body and can implement opening and closing, the clamping jaw having a plurality of jaw portions which are circumferentially distributed and can be inserted into the corresponding grooves, and the number of the grooves being a multiple of that of the jaw portions.

A frame body is disposed on the workbench, and the moving seat can be disposed on the frame body.

In the intelligent microbial sample treatment system, the grabbing assembly comprises a vacuum sucker disposed at the bottom of the rotating body and a pipeline structure communicating with the vacuum sucker and used for vacuum suction, and the bottom of the sucker is higher than that of the protrusion.

In the intelligent microbial sample treatment system, the pipeline structure comprises a passage vertically formed in the rotating body, a first connector connected to the upper end of the passage and a second connector connected to the lower end of the passage, and the vacuum sucker communicates with the second connector.

In the intelligent microbial sample treatment system, the bottom of the rotating body has a concave cavity communicating with the passage, and the vacuum sucker is disposed in the concave cavity.

In the intelligent microbial sample treatment system, the sucker and the rotating body are coaxially disposed, and the passage and the rotating body are coaxially disposed.

In the intelligent microbial sample treatment system, the moving seat has a mounting hole vertically disposed, the rotating body has a rotating shaft extending into the mounting hole, and a bearing located in the mounting hole is disposed between the rotating shaft and the moving seat.

In the intelligent microbial sample treatment system, the power assembly comprises a motor disposed on the moving seat, a driving gear disposed on an output shaft of the motor and a driven gear disposed on the rotating shaft, and the driving gear is meshed with the driven gear.

Compared to the prior art, the intelligent microbial sample treatment system has the following advantages:

the culture medium loading rotary table is provided with a plurality of loading grooves, transmission of a plurality of culture media can be simultaneously carried out so as to reduce space occupation while improving the working efficiency, and the loading station, the streaking station and the label printing station are distributed on the culture medium streaking rotary table so as to further reduce space occupation; the structural layout is reasonable, the first-region streaking module, the second-region streaking module, the first driving structure and the second driving structure cannot collide with each other, and the working process is stable and reliable; due to arrangement of the Y-axis guide rail, the second placement seat can be effectively guided to enable the second placement seat and the first driving structure to simultaneously act, the travel of the first driving structure is reduced, and time is saved, thereby improving the working efficiency; and the guide door is disposed on the sample input rail, so that the unqualified sample cup can be prevented from being input.

Figure 1:
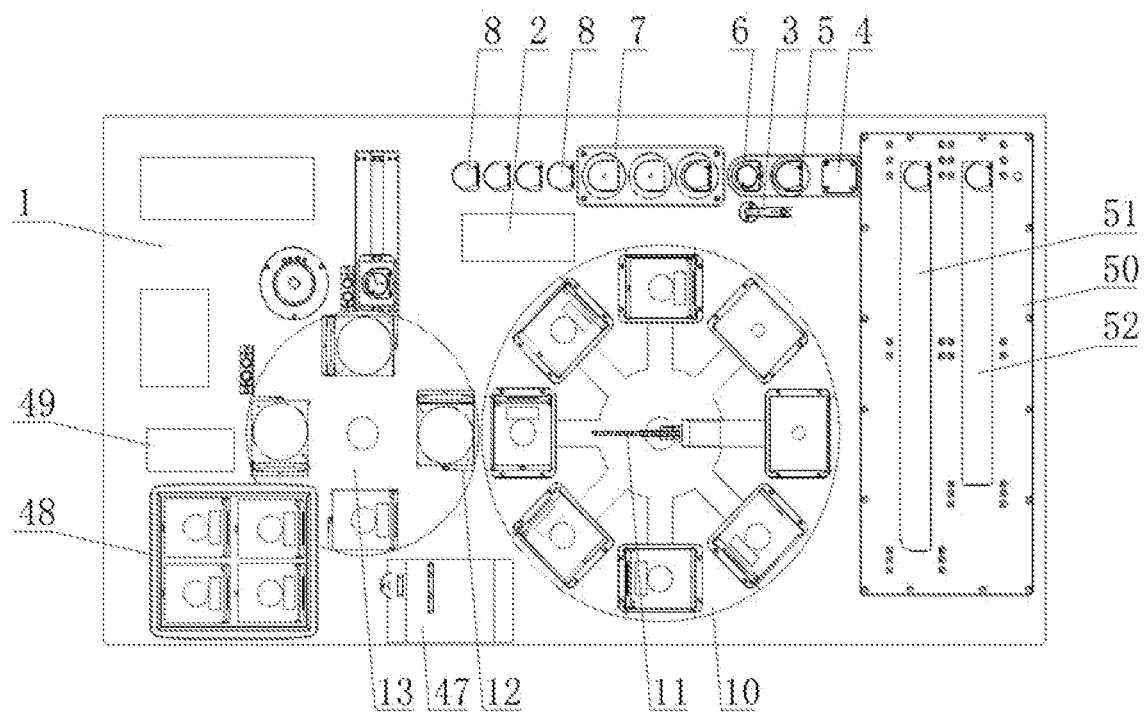
FIG. 1 is a diagram of a plane layout of a preferred embodiment provided by the present invention.

In the drawings, 1, workbench; 2, sample transfer device; 3, filling device; 4, scanning device; 5, weight detection device; 6, filling location; 7, shaking device; 8, waiting location; 9, sample cup; 10, culture medium loading rotary table; 11, pushing device; 12, opening device; 13, culture medium streaking rotary table; 14, first side plate; 15, second side plate; 16, backing plate; 17, positioning protrusion; 18, first mounting groove; 19, second mounting groove; 20, limiting blocking edge; 21, gap; 22, front plate; 23, elastic limiting plate; 24, pressure plate; 25, screw; 26, first guide rail; 27, second guide rail; 28, first-region streaking module; 29, second-region streaking module; 30, first placement seat; 31, second placement seat; 32, grabbing device; 33, sterilizer; 34, support pillar; 35, X-axis guide rail; 36, first sliding seat; 37, first power unit, 38, Z-axis guide rail; 39, second sliding seat; 40, second power unit; 41, Y-axis guide rail; 42, third sliding seat; 43, needle seat; 431, counter weight block; 44, via hole; 45, inoculation needle body; 46, floating avoiding hole; 47, label printer; 48, culture medium storage box; 49, boxing module; 50, sample cup transmission device; 51, sample input rail; 52, abnormal sample output rail; 53, guide door; 54, moving seat; 55, rotating body; 56, protrusion; 57, vacuum sucker; 58, passage; 59, first connector; 60, second connector; 61, concave cavity; 62, mounting hole; 63, rotating shaft; 91, cup body; 92, cup cover; 93, positioning plane; and 94, groove.

DETAILED DESCRIPTION OF THE EMBODIMENTS

The followings are specific embodiments of the present invention and the technical solutions of the present invention will be further described in combination with the drawings, but the present invention is not limited to these embodiments.

Embodiment 1

As shown in FIG. 1, an intelligent microbial sample treatment system comprises a workbench 1, and a sample treatment assembly, a culture medium treatment assembly, a streaking assembly and a culture medium storage assembly which are disposed on the workbench 1. The sample treatment assembly comprises a sample transfer device 2, a filling device 3, and a scanning device 4, a weight detection device 5, a filling location 6, a shaking device 7 and waiting locations 8 which are disposed in sequence along a same straight line, the scanning device 4 is used for scanning a code disposed on the outer side of a sample cup 9, the weight detection device 5 is used for measuring the overall weight of the sample cup, the filling device 3 is used for filling a sample treatment agent into the sample cup 9 at the filling location 6, the shaking device 7 is used for shaking and uniformly mixing the treatment agent and a sample in the sample cup 9, the waiting locations 8 are used for placing the sample cup 9 after the shaking and uniformly mixing, and the sample transfer device 2 moves a sample box among the scanning device 4, the weight detection device 5, the filling location 6, the shaking device 7 and the waiting locations 8.

As shown in FIG. 1, the culture medium treatment assembly comprises a culture medium loading rotary table 10 with loading grooves, a pushing device 11, an opening device 12 and a culture medium streaking rotary table 13 with station grooves, the culture medium loading rotary table 10 is located in front of the sample treatment assembly, the culture medium streaking rotary table 13 is located beside the culture medium loading rotary table 10, and when the culture medium streaking rotary table 13 rotates, the station grooves are sequentially close to the culture medium loading rotary table 10, the streaking assembly and the culture medium storage assembly.

In this embodiment, N (N≥2) loading grooves are provided and distributed on the culture medium loading rotary table 10 in an annular array, and n (n≥2) station grooves are provided and distributed on the culture medium streaking rotary table 13 in an annular array; the station groove directly facing the loading groove is located at a loading station, and the pushing device 11 is used for pushing a culture medium box in the loading groove into the station groove at the loading station; and the opening device 12 is located at the upper portion of the station groove and used for opening the culture medium box entering the station groove. The culture medium loading rotary table 10 carries out stepping rotation according to an angle of 360°/N, the culture medium streaking rotary table carries out stepping rotation according to an angle of 360°/n, and every time when the culture medium loading rotary table 10 and the culture medium streaking rotary table 13 rotate, there is one station groove directly facing the loading groove.

Figure 2:
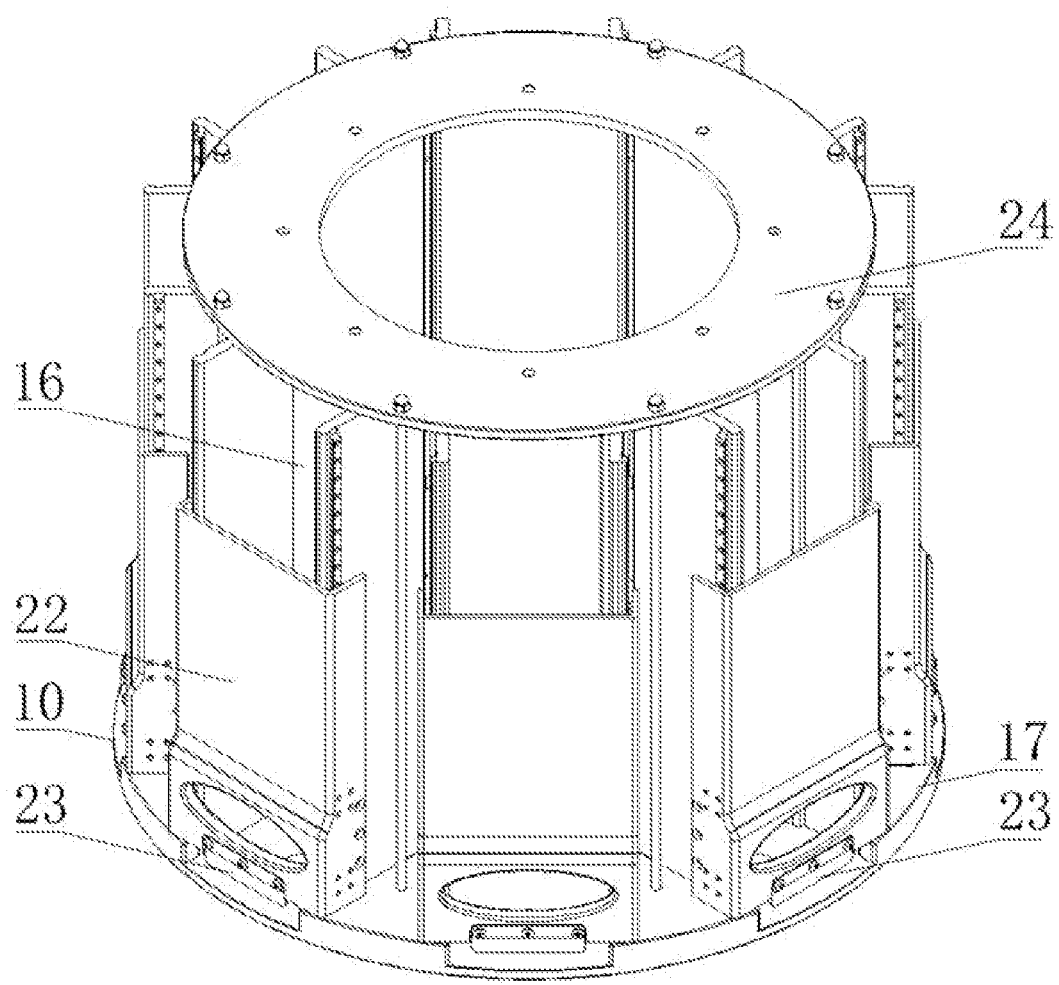
FIG. 2 is a structural schematic diagram of a culture medium loading rotary table provided by the present invention.
Figure 3:
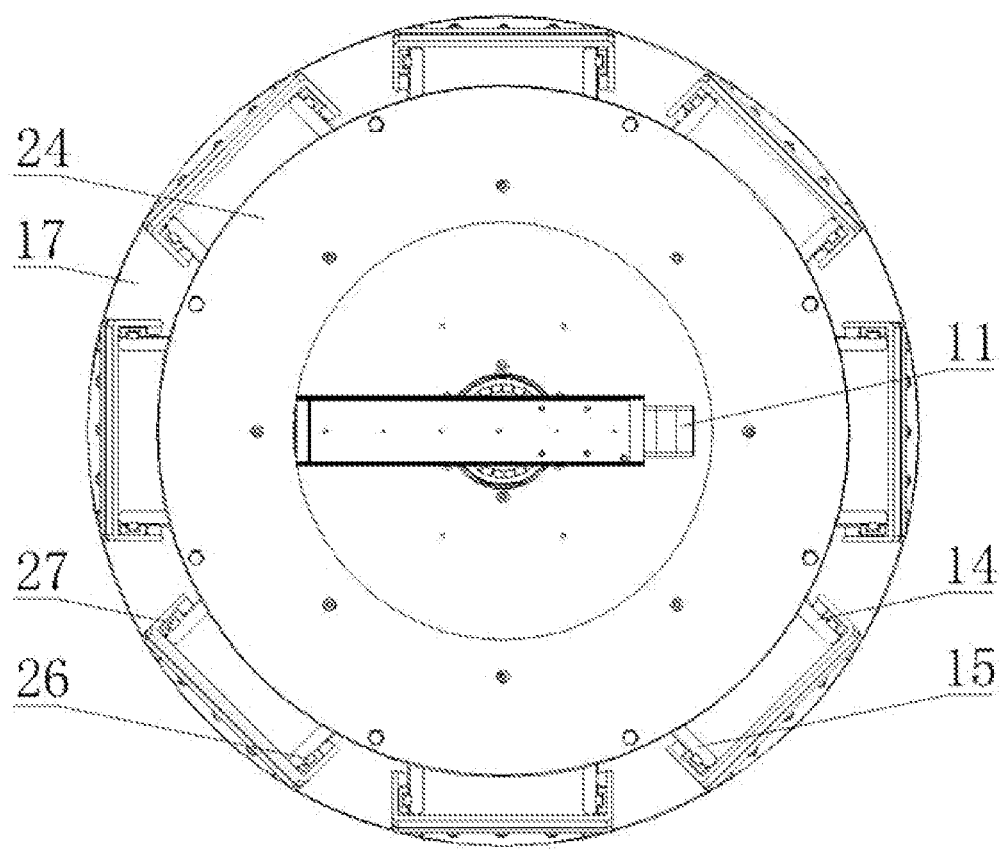
FIG. 3 is a top view of a culture medium loading rotary table provided by the present invention.

As shown in FIG. 2 and FIG. 3, the loading groove is formed by a first side plate 14, a second side plate 15 and a backing plate 16, the culture medium loading rotary table 10 is provided with a positioning structure for positioning the first side plate 14, the second side plate 15 and the backing plate 16, and the backing plate 16 is provided with a penetrating hole for the pushing device 11 to penetrate. A plurality of culture medium boxes can be placed in a stacking manner in each loading groove from top to bottom, and the pushing device 11 ejects out one culture medium box each time.

Figure 4:
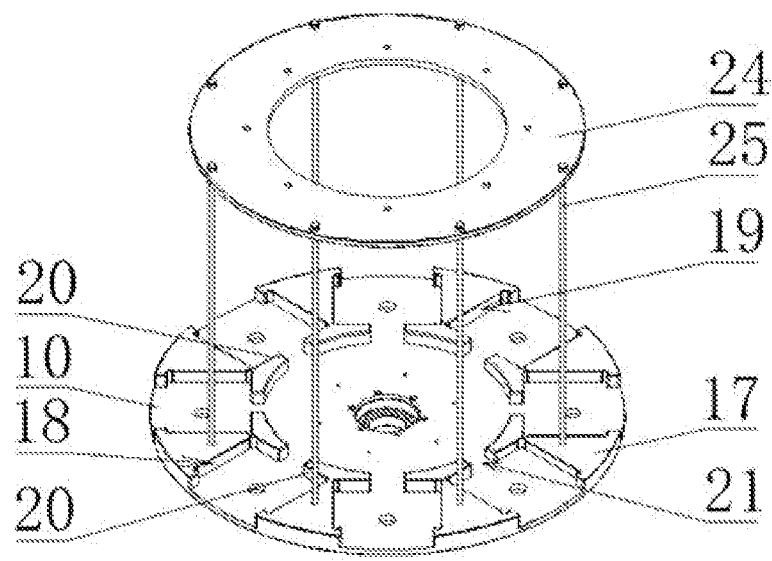
FIG. 4 is an internal structural schematic diagram of a culture medium loading rotary table provided by the present invention.

As shown in FIG. 4, the positioning structure comprises a plurality of positioning protrusions 17 separately positioned between two adjacent loading grooves, one side of the positioning protrusion 17 is provided with a first mounting groove 18 for mounting the first side plate 14, the other side of the positioning protrusion 17 is provided with a second mounting groove 19 for mounting the second side plate 15, one end, close to the central axis of the culture medium loading rotary table 10, of the positioning protrusion 17 is provided with a limiting blocking edge 20, one side, facing the central axis of the culture medium loading rotary table 10, of the backing plate 16 is attached to the limiting blocking edge 20, and a gap 21 for the pushing device 11 to pass through is provided between two adjacent limiting blocking edges 20. During mounting, firstly, the backing plate 16 is inserted between two positioning protrusions 17, the backing plate 16 is attached to the limiting blocking edge 20, the first side plate 14 is inserted into the first mounting groove 18, the second side plate 15 is inserted into the second mounting groove 19, the first side plate 14 and the second side plate 15 are pressed against the backing plate 16, and the backing plate 16 is prevented from falling off under the pressing-against action of the first side plate 14 and the second side plate 15. In order to improve stability, the first side plate 14, the second side plate 15 and the backing plate 16 are connected as a whole.

As shown in FIG. 2 and FIG. 3, one end, away from the central axis of the culture medium loading rotary table 10, of the loading groove is provided with a front plate 22 of which the lower end is pressed against the positioning protrusion 17, the front plate 22 is provided with an elastic limiting plate 23 extending into the loading groove, and the distance from the lower end of the elastic limiting plate 23 to the bottom of the loading groove is less than the thickness of the culture medium box. The first side plate 14 is provided with a first guide rail 26, the second side plate 15 is provided with a second guide rail 27, and the front plate 22 is slidably disposed on the first guide rail 26 and the second guide rail 27.

Figure 5:
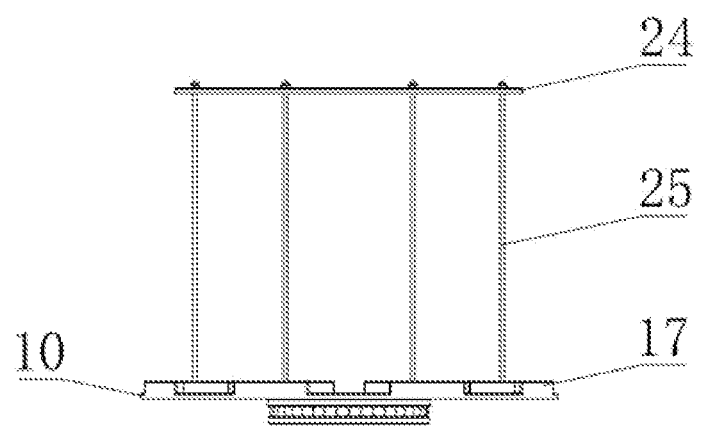
FIG. 5 is a side view of FIG. 4 provided by the present invention.

As shown in FIG. 5, the positioning structure further comprises a pressure plate 24 simultaneously pressing the upper ends of the first side plate 14, the second side plate 15 and the backing plate 16 and a plurality of screws 25 for fixing the pressure plate 24 to the culture medium loading rotary table, the screws 25 are disposed perpendicular to the culture medium loading rotary table 10, and the lower ends of the screws 25 are connected to the positioning protrusions 17. In order to improve stability, the first side plate 14, the second side plate 15 and the backing plate 16 are connected as a whole.

Figure 6:
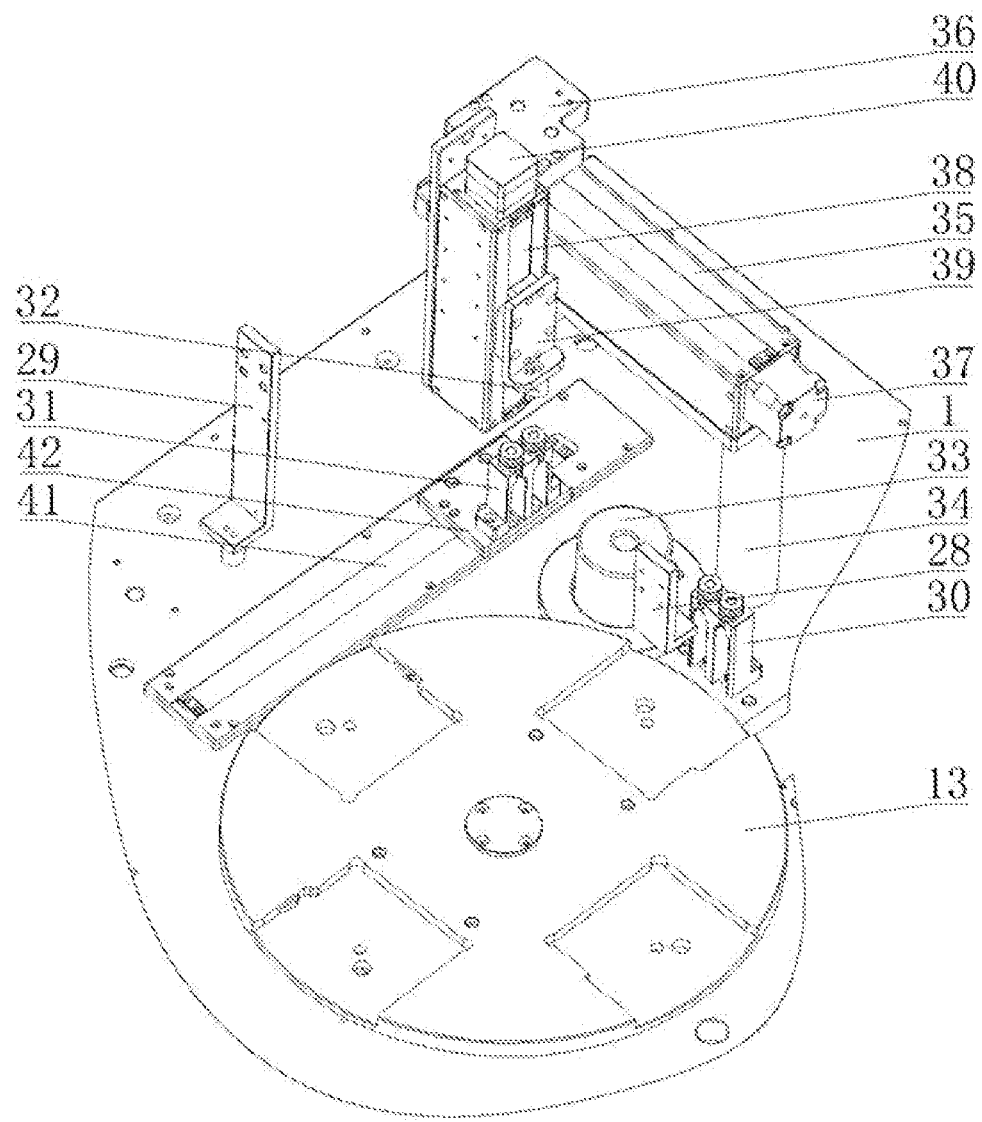
FIG. 6 is a structural schematic diagram of a streaking assembly provided by the present invention.

As shown in FIG. 6, the streaking assembly comprises a first-region streaking module 28, a second-region streaking module 29, a first placement seat 30 located within the working range of the first-region streaking module 28 and a second placement seat 31 located within the working range of the second-region streaking module 29, the workbench 1 is provided with a first driving structure, a grabbing device 32 which is driven by the first driving structure and can move along an X axis and a Z axis and a sterilizer 33 located in a movement region of the grabbing device 32, the first placement seat 30 is located in the movement region of the grabbing device 32, and the workbench 1 is further provided with a second driving structure for driving the second placement seat 31 to move between the working range of the second-region streaking module 29 and the movement region of the grabbing device 32.

When an inoculation needle in the first placement seat 30 is disinfected, the grabbing device 32 grabs the inoculation needle located in the first placement seat 30, the inoculation needle is enabled to move into the sterilizer 33 to be disinfected under the action of the first driving structure, and after disinfection is completed, the inoculation needle is returned to the first placement seat 30 under the action of the first driving structure and the grabbing device 32. When an inoculation needle in the second placement seat 31 is disinfected, the second driving structure drives the second placement seat 32 to move into the movement region of the grabbing device 32, the grabbing device 32 grabs the inoculation needle located in the second placement seat 31, the inoculation needle is enabled to move into the sterilizer 33 to be disinfected under the action of the first driving structure, after disinfection is completed, the inoculation needle is returned to the second placement seat 31 under the action of the first driving structure and the grabbing device 32, and subsequently the second placement seat 31 is returned to the working range of the second-region streaking module 29 under the action of the second driving structure.

As shown in FIG. 6, the first driving structure comprises a support pillar 34 disposed on the workbench 1, an X-axis guide rail 35 disposed on the support pillar 34, a first sliding seat 36 slidably disposed on the X-axis guide rail 35, a first power unit 37 for driving the first sliding seat 36 to slide, a Z-axis guide rail 38 disposed on the first sliding seat 36, a second sliding seat 39 slidably disposed on the Z-axis guide rail 38 and a second power unit 40 for driving the second sliding seat 39 to slide, and the grabbing device 32 is disposed on the second sliding seat 39. The X-axis guide rail 35 horizontally extends, and the Z-axis guide rail 38 is vertically disposed beside the X-axis guide rail 35. When the first power unit 37 works, the first sliding seat 36 is driven to horizontally move on the X-axis guide rail 35; and when the second power unit 40 works, the second sliding seat 39 is driven to vertically move on the Z-axis guide rail 38;

wherein, the first power unit 37 is a motor, and the motor is in transmission connection with the first sliding seat 36 by a first ball screw pair; and the second power unit 40 is a motor, and the motor is in transmission connection with the second sliding seat 39 by a second ball screw pair.

Figure 7:
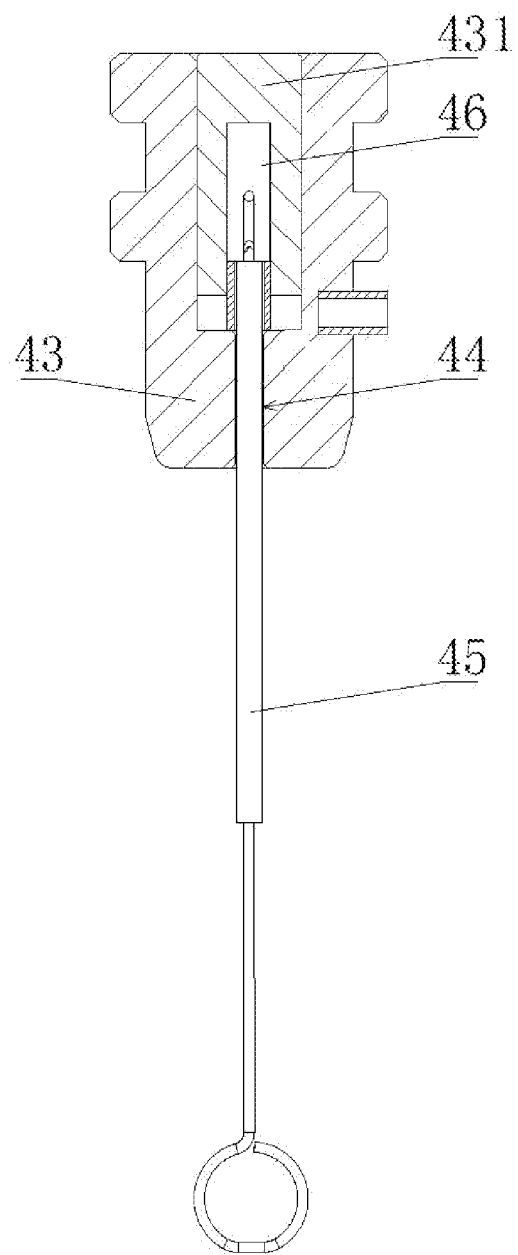
FIG. 7 is a structural schematic diagram of an inoculation needle provided by the present invention.

As shown in FIG. 6, the second driving structure comprises a Y-axis guide rail 41 disposed on the workbench 1, a third sliding seat 42 disposed on the Y-axis guide rail 41 and a third power unit for driving the third sliding seat 42 to slide, one end of the Y-axis guide rail 41 is located in the movement region of the grabbing device 32, the other end of the Y-axis guide rail 41 is located within the working range of the second-region streaking module 29, and the second placement seat 31 is disposed on the third sliding seat 42. When the third power unit is a motor, the motor is in transmission connection with the third sliding seat 42 by a third ball screw pair. When the second placement seat 31 moves into the movement region of the grabbing device 32, the sterilizer 33 is located between the first placement seat 30 and the second placement seat 31. Due to arrangement of the Y-axis guide rail 41, the second placement seat 31 can be effectively guided to enable the second placement seat 31 and the first driving structure to simultaneously act, the travel of the first driving structure is reduced, and time is saved, thereby improving the working efficiency;

wherein, the grabbing device 32 is an electromagnet, the inoculation needle grabbed by the grabbing device 32 comprises a needle seat 43, as shown in FIG. 7, a via hole 44 is disposed in the needle seat 43, an inoculation needle body 45 capable of moving in the axial direction of the via hole 44 is disposed in a penetrating manner in the via hole 44, the lower end of the inoculation needle body 45 penetrates out of the lower end of the via hole 44, the upper end of the inoculation needle body 45 penetrates out of the upper end of the via hole 44, a counter weight block 431 for preventing the inoculation needle body 45 from falling out of the via hole 44 is disposed between the inoculation needle body 45 and the needle seat 43, and the needle seat 43 has magnetism, wherein the counter weight block 431 is located above the via hole 44, the maximum lateral size of the counter weight block 431 is larger than the hole diameter of the via hole 44, and a floating avoiding hole 46 is disposed in the counter weight block 431.

As shown in FIG. 1, the culture medium storage assembly comprises a label printer 47, a culture medium storage box 48 and a boxing module 49, the station groove disposed opposite to the label printer 47 is located at a label printing station, the culture medium storage box 48 is located between a streaking station and the label printing station and partially extends to the position above the culture medium streaking rotary table 13, the culture medium storage box 48 is provided with a closing mechanism for closing the culture medium box moving to the label printing station from the streaking station, and the boxing module 49 is used for moving the culture medium box between the label printing station and the culture medium storage box 48.

Figure 8:
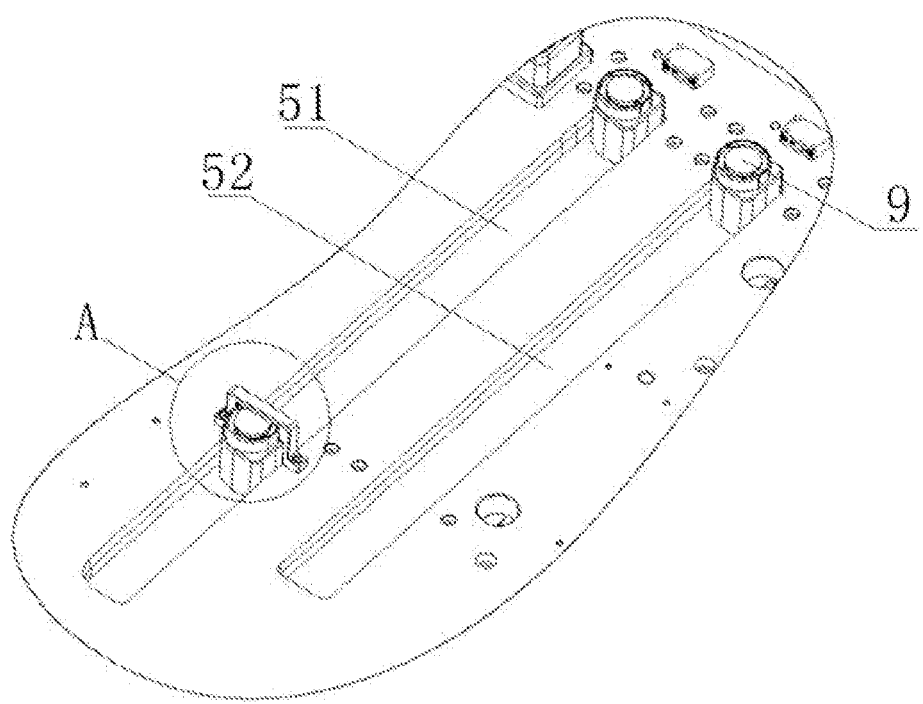
FIG. 8 is a partial schematic diagram of a sample cup transmission device provided by the present invention.
Figure 9:
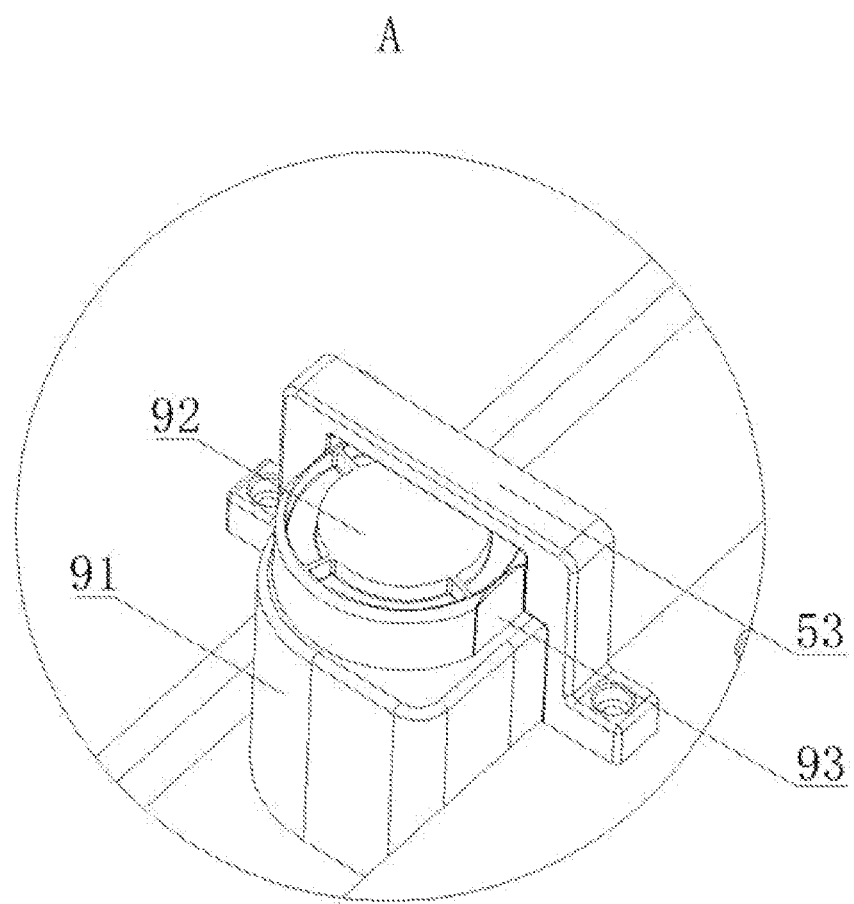
FIG. 9 is an enlarged schematic diagram of a position A in FIG. 8 provided by the present invention.

As shown in FIG. 9, the sample cup 9 comprises a cup body 91 and a cup cover 92, and the outer wall of the cup cover 92 has a positioning plane 93 vertically extending. As shown in FIGS. 1 and 8, the workbench 1 is provided with a sample cup transmission device 50, the sample cup transmission device 50 is provided with a sample input rail 51 and an abnormal sample output rail 52, the sample input rail 51 is provided with a guide door 53, the inner side of the guide door 53 has a limiting plane vertically extending along the conveying direction of the sample input rail 51, and the minimum distance from the central axis of the cup cover 92 of the sample cup 9 located in the sample input rail 51 to the limiting plane is equal to the distance from the positioning plane 93 to the central axis of the cup cover 92.

After the cup body 91 is placed into the sample input rail 51, the cup body 91 cannot circumferentially rotate. When the sample cup 9 qualified in matching of the cup cover 92 and the cup body 91 passes through the guide door 53, the positioning plane 93 is parallel to the limiting plane without interference and obstruction therebetween, and the sample cup 9 can pass through the guide door 53; and when the sample cup 9 unqualified in matching of the cup cover 92 and the cup body 91 passes through the guide door 53, the positioning plane 93 is not parallel to the limiting plane, interference and obstruction can be generated therebetween, and the guide door 53 prevents the sample cup 9 from passing through.

Figure 10:
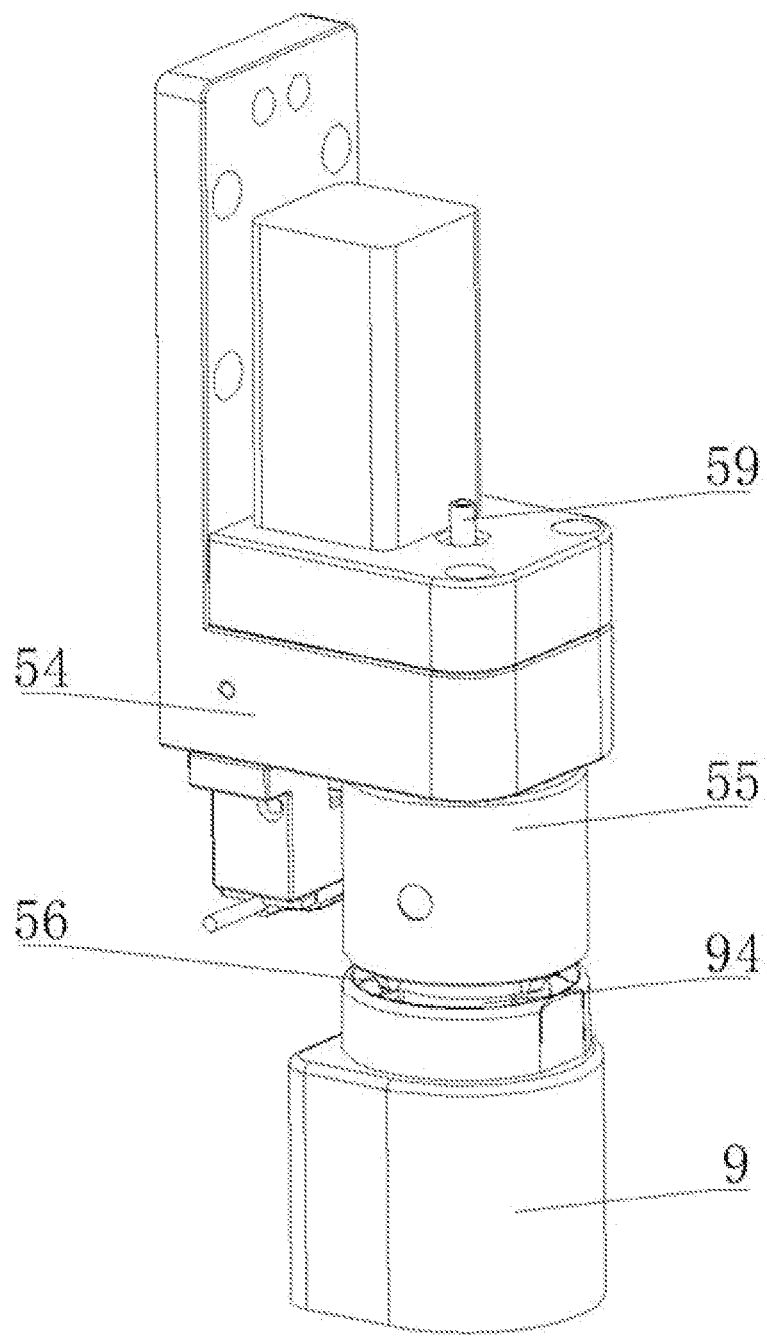
FIG. 10 is a structural schematic diagram of a sample cup opening and closing device provided by the present invention.
Figure 11:
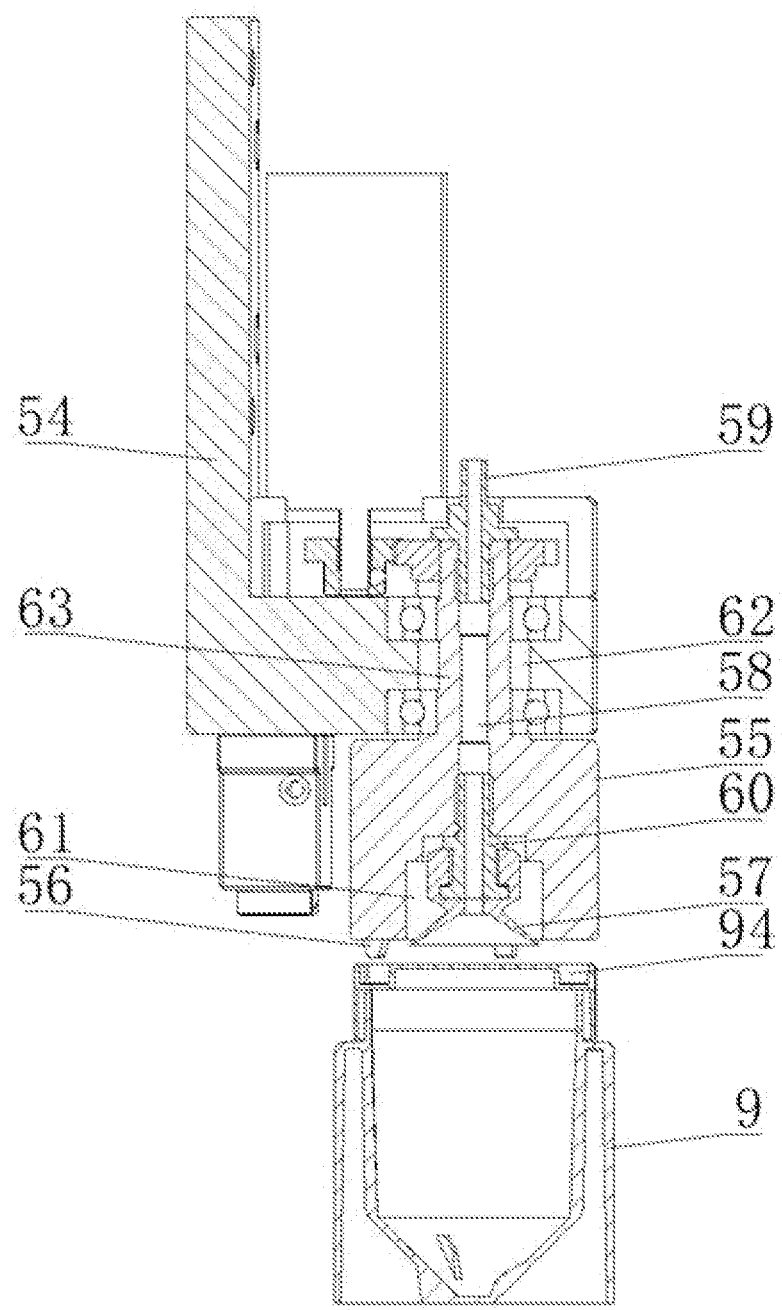
FIG. 11 is a section view of a sample cup opening and closing device provided by the present invention.

As shown in FIG. 10 and FIG. 11, the top of the cup cover 92 of the sample cup 9 has a plurality of grooves 94 circumferentially distributed, the workbench 1 is also provided with a sample cup opening and closing device, and the sample cup opening and closing device comprises a moving seat 54, a rotating body 55 vertically disposed in a penetrating manner in the moving seat 54, and a power assembly for driving the rotating body 55 to rotate around the central axis per se; and the sample cup opening and closing device further comprises the following structures:

a plurality of protrusions 56 which are circumferentially distributed at the bottom of the rotating body 55 and can be inserted into the corresponding grooves 94, the number of the grooves 94 being larger than or equal to that of the protrusions 56, each protrusion 56 having one groove 94 corresponding to the protrusion 56, and the rotating body 55 being further provided with a grabbing assembly.

A frame body is disposed on the workbench 1, and the moving seat 54 can be disposed on the frame body.

As shown in FIG. 11, the grabbing assembly comprises a vacuum sucker 57 disposed at the bottom of the rotating body 55 and a pipeline structure communicating with the vacuum sucker 57 and used for vacuum suction, and the bottom of the sucker is higher than that of the protrusion 56.

As shown in FIG. 11, the pipeline structure comprises a passage 58 vertically disposed in the rotating body 55, a first connector 59 connected to the upper end of the passage 58 and a second connector 60 connected to the lower end of the passage 58, and the vacuum sucker 57 communicates with the second connector 60.

As shown in FIG. 11, the bottom of the rotating body 55 has a concave cavity 61 communicating with the passage 58, and the vacuum sucker 57 is disposed in the concave cavity 61, wherein the sucker and the rotating body 55 are coaxially disposed, and the passage 58 and the rotating body 55 are coaxially disposed.

As shown in FIG. 11, the moving seat 54 has a mounting hole 62 vertically disposed, the rotating body 55 has a rotating shaft 63 extending into the mounting hole 62, and a bearing located in the mounting hole 62 is disposed between the rotating shaft 63 and the moving seat 54.

As shown in FIGS. 10 and 11, the power assembly comprises a motor disposed on the moving seat 54, a driving gear disposed on an output shaft of the motor and a driven gear disposed on the rotating shaft 63, and the driving gear is meshed with the driven gear.

The working steps of the intelligent microbial sample treatment system are as follows:

1. the system is started, the sample box is manually/automatically placed into the sample input rail 51, the unqualified sample cups are screened by the guide door 53, and the qualified sample cups move in place under the transmission of the sample input rail 51; and the culture medium loading rotary table 10 rotates, the culture medium streaking rotary table 13 rotates anticlockwise, the culture medium boxes are manually/automatically and sequentially placed into the loading grooves one by one, and each loading groove has a plurality of culture medium boxes disposed in a stacking manner;
2. the sample transfer device 2 grabs the sample cups to the position of the scanning device 4 from the sample input rail 51, the scanning device 4 carries out scanning on the codes on the sample cups, and if the codes are incorrect, the sample cups are grabbed onto the abnormal sample output rail 52 by the sample transfer device 2 and output by the abnormal sample output rail 52;
3. the sample cups with the correct codes in the step 2 move to the position of the weight detection device 5 under the action of the sample transfer device 2, the weights of the sample cups are measured, if the weights are unqualified, the sample cups are grabbed onto the abnormal sample output rail 52 by the sample transfer device 2 and output by the abnormal sample output rail 52, and the sample cups with the qualified weights are transported to the filling location 6 by the sample transfer device 2;
4. the sample cups located at the filling location 6 are filled with the sample treatment agent by the filling device 3;
5. the sample cups obtained in the step 4 are fed into the shaking device 7, and the treatment agent and samples in the sample cups are shaken and uniformly mixed;
6. the sample cups obtained in the step 5 are fed to the waiting locations 8;
7. When it is detected that there are the sample cups at the waiting locations 8, the pushing device 11 pushes the culture medium box into the loading station, during pushing, the opening device 12 opens the culture medium box, and the culture medium streaking rotary table 13 rotates anticlockwise to take the culture medium box to the streaking station;
8. after the inoculation needle is disinfected by the streaking assembly and is dipped into the sample in the sample cup, streaking is carried out on the culture medium box; and
9. the streaked culture medium box rotates along with the culture medium streaking rotary table 13, is closed under the action of the culture medium storage box 48 and moves to the label printing station, and code marking is carried out on the culture medium box by the label printer 47; and the code-marked culture medium box is transferred into the culture medium storage box 48 by the boxing module 49.

In this embodiment, the sample transfer device 2, the first-region streaking module 28, the second-region streaking module 29 and the boxing module 49 are manipulators.

Embodiment 2

The structure principle of this embodiment is basically the same as that of Embodiment 1, and the differences lie in that in the streaking assembly, the first power unit 37 is a cylinder, and a piston rod of the cylinder is fixedly connected with the first sliding seat 36; the second power unit 40 is a cylinder, and a piston rod of the cylinder is fixedly connected with the first sliding seat 36; the third power unit is a cylinder, and a piston rod of the cylinder is fixedly connected with the third sliding seat 42.

Embodiment 3

The structure principle of this embodiment is basically the same as that of Embodiment 1, and the differences lie in that the workbench 1 is also provided with the sample cup opening and closing device, and the sample cup opening and closing device comprises the moving seat 54, the rotating body 55 vertically disposed in a penetrating manner in the moving seat 54, and the power assembly for driving the rotating body 55 to rotate around the central axis per se. The sample cup opening and closing device further comprises the following structure: a clamping jaw which is disposed at the bottom of the rotating body 55 and can implement opening and closing, the clamping jaw having a plurality of jaw portions which are circumferentially distributed and can be inserted into the corresponding grooves 94, and the number of the grooves 94 being a multiple of that of the jaw portions.

The specific embodiments described herein are merely used for illustrating the spirit of the present invention. Those skilled in the art of the present invention can make various modifications or supplementations to the described specific embodiments or adopt similar modes for replacement of the described specific embodiments, but cannot depart from the spirit of the present invention or go beyond the scope defined by the appended claims.

What is claimed is:

1. An microbial sample treatment system, comprising
a workbench,
a sample treatment assembly,
a culture medium treatment assembly,
a streaking assembly and
a culture medium storage assembly,
wherein the sample treatment assembly, the culture medium treatment assembly, the streaking assembly and the culture medium storage assembly are disposed on the workbench;
the culture medium treatment assembly comprises a culture medium loading rotary table with loading grooves, a pushing device and a culture medium streaking rotary table with station grooves, wherein the culture medium loading rotary table is located in front of the sample treatment assembly, the culture medium streaking rotary table is located beside the culture medium loading rotary table, and when the culture medium streaking rotary table rotates, the station grooves are sequentially close to the culture medium loading rotary table, the streaking assembly and the culture medium storage assembly.

2. The microbial sample treatment system of claim 1, wherein a number of the loading grooves is N and a number of the station grooves is n; the loading grooves are provided and distributed on the culture medium loading rotary table in a first annular array, and the station grooves are provided and distributed on the culture medium streaking rotary table in a second annular array; a station groove directly facing a loading groove is located at a loading station, and the pushing device is used for pushing a culture medium box in the loading groove into the station groove at the loading station.

3. The microbial sample treatment system of claim 2, wherein the loading groove is formed by a first side plate, a second side plate and a backing plate; the culture medium loading rotary table is provided with a positioning structure for positioning the first side plate, the second side plate and the backing plate, and the backing plate is provided with a penetrating hole for the pushing device to penetrate.

4. The microbial sample treatment system of claim 3, wherein the positioning structure comprises a plurality of positioning protrusions separately located between two adjacent loading grooves, wherein
a first side of each of the positioning protrusions is provided with a first mounting groove for mounting the first side plate,
a second side of each of the positioning protrusions is provided with a second mounting groove for mounting the second side plate,
one end, close to a central axis of the culture medium loading rotary table, of each of the positioning protrusions is provided with a limiting blocking edge,
one side, facing the central axis of the culture medium loading rotary table, of the backing plate is attached to the limiting blocking edge, and a gap for the pushing device to pass through is provided between two adjacent limiting blocking edges.

5. The microbial sample treatment system of claim 4, wherein one end, away from the central axis of the culture medium loading rotary table, of the loading groove is provided with a front plate, wherein a lower end of the front plate is pressed against one of the positioning protrusions, the front plate is provided with an elastic limiting plate extending into the loading groove, and a distance from a lower end of the elastic limiting plate to a bottom of the loading groove is less than a thickness of the culture medium box.

6. The microbial sample treatment system of claim 1, wherein the streaking assembly comprises a first-region streaking module, a second-region streaking module, a first placement seat located within a working range of the first-region streaking module and a second placement seat located within a working range of the second-region streaking module,
the workbench is provided with a first driving structure, wherein a grabbing device is driven by the first driving structure and moves along an X axis and a Z axis, and a sterilizer located in a movement region of the grabbing device,
the first placement seat is located in the movement region of the grabbing device, and the workbench is further provided with a second driving structure for driving the second placement seat to move between the working range of the second-region streaking module and the movement region of the grabbing device.

7. The microbial sample treatment system of claim 6, wherein the first driving structure comprises a support pillar disposed on the workbench, an X-axis guide rail disposed on the support pillar, a first sliding seat slidably disposed on the X-axis guide rail, a first power unit for driving the first sliding seat to slide, a Z-axis guide rail disposed on the first sliding seat, a second sliding seat slidably disposed on the Z-axis guide rail and a second power unit for driving the second sliding seat to slide, and the grabbing device is disposed on the second sliding seat.

8. The microbial sample treatment system of claim 7, wherein the second driving structure comprises a Y-axis guide rail disposed on the workbench, a third sliding seat disposed on the Y-axis guide rail and a third power unit for driving the third sliding seat to slide, a first end of the Y-axis guide rail is located in the movement region of the grabbing device, a second end of the Y-axis guide rail is located within the working range of the second-region streaking module, and the second placement seat is disposed on the third sliding seat.

9. The microbial sample treatment system of claim 1, wherein the culture medium storage assembly comprises a label printer and a culture medium storage box, a station groove disposed opposite to the label printer is located at a label printing station, the culture medium storage box is located between a streaking station and the label printing station and partially extends to a position above the culture medium streaking rotary table.

10. The microbial sample treatment system of claim 1, wherein the sample cup comprises a cup body and a cup cover, and an outer wall of the cup cover has a positioning plane vertically extending; the workbench is provided with a sample cup transmission device, the sample cup transmission device is provided with a sample input rail and an abnormal sample output rail, the sample input rail is provided with a guide door, an inner side of the guide door has a limiting plane vertically extending along a conveying direction of the sample input rail, and a minimum distance from a central axis of the cup cover of the sample cup located in the sample input rail to the limiting plane is equal to a distance from the positioning plane to the central axis of the cup cover.

11. The microbial sample treatment system of claim 1, wherein the sample cup comprises a cup body and a cup cover, a top of the cup cover has a plurality of grooves circumferentially distributed, the workbench is also provided with a sample cup opening and closing device, and the sample cup opening and closing device comprises a moving seat, a rotating body vertically disposed in a penetrating manner in the moving seat, and a power assembly for driving the rotating body to rotate around a central axis per se.

12. The microbial sample treatment system of claim 11, wherein the grabbing assembly comprises a vacuum sucker disposed at the bottom of the rotating body and a pipeline structure communicating with the vacuum sucker and used for vacuum suction, and a bottom of the vacuum sucker is higher than a bottom of the protrusions.

13. The microbial sample treatment system of claim 12, wherein the pipeline structure comprises a passage vertically disposed in the rotating body, a first connector connected to an upper end of the passage and a second connector connected to a lower end of the passage, and the vacuum sucker communicates with the second connector.

14. The microbial sample treatment system of claim 13, wherein the bottom of the rotating body has a concave cavity communicating with the passage, and the vacuum sucker is disposed in the concave cavity.

15. The microbial sample treatment system of claim 14, wherein the vacuum sucker and the rotating body are coaxially disposed, and the passage and the rotating body are coaxially disposed.

16. The microbial sample treatment system of claim 13, wherein the vacuum sucker and the rotating body are coaxially disposed, and the passage and the rotating body are coaxially disposed.

17. The microbial sample treatment system of claim 12, wherein the moving seat has a mounting hole vertically disposed, the rotating body has a rotating shaft extending into the mounting hole, and a bearing located in the mounting hole is disposed between the rotating shaft and the moving seat.

18. The microbial sample treatment system of claim 17, wherein the power assembly comprises a motor disposed on the moving seat, a driving gear disposed on an output shaft of the motor and a driven gear disposed on the rotating shaft, and the driving gear is meshed with the driven gear.

* * * * *